US007850632B2

(12) United States Patent
Gilmour

(10) Patent No.: US 7,850,632 B2
(45) Date of Patent: *Dec. 14, 2010

(54) KNEE BRACE HAVING AN ADAPTABLE THIGH PAD

(75) Inventor: Robert Gilmour, Vista, CA (US)

(73) Assignee: VQ OrthoCare, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/981,858

(22) Filed: Nov. 5, 2004

(65) Prior Publication Data

US 2006/0100561 A1    May 11, 2006

(51) Int. Cl.
*A61F 5/00* (2006.01)
*A61F 5/37* (2006.01)
*A61F 11/00* (2006.01)

(52) U.S. Cl. .............................. 602/26; 602/5; 602/12; 602/16; 602/23; 128/846; 128/869; 128/878; 128/882

(58) Field of Classification Search .................. 602/26, 602/16, 23, 5, 12, 25–27, 60–62; 128/845, 128/846, 869, 882, DIG. 15; 2/22, 24; 24/327, 24/336
See application file for complete search history.

(56) References Cited

U.S. PATENT DOCUMENTS

| 1,092,836 | A | * | 4/1914 | Hart ................................. 2/22 |
| 4,686,969 | A | | 8/1987 | Scott |
| 4,803,975 | A | * | 2/1989 | Meyers ........................ 602/26 |
| 4,928,670 | A | | 5/1990 | DeLorenzo |
| 4,969,452 | A | | 11/1990 | Petrofsky et al. |
| 5,302,169 | A | | 4/1994 | Taylor |
| 5,336,161 | A | | 8/1994 | Lengyel |
| 5,383,845 | A | | 1/1995 | Nebolon |
| 5,400,806 | A | | 3/1995 | Taylor |
| D372,983 | S | | 8/1996 | Nebolon |
| 5,571,206 | A | * | 11/1996 | Varn ............................. 623/27 |
| 5,713,837 | A | | 2/1998 | Grim et al. |
| 5,743,865 | A | | 4/1998 | Townsend |
| 5,885,235 | A | | 3/1999 | Opahle et al. |
| 5,888,235 | A | | 3/1999 | Jacobsen et al. |
| 5,954,677 | A | | 9/1999 | Albrecht et al. |
| 6,024,713 | A | * | 2/2000 | Barney ......................... 602/23 |
| RE37,297 | E | * | 7/2001 | Smith ........................... 602/26 |
| 6,290,664 | B1 | * | 9/2001 | Nauert ......................... 602/16 |
| 6,331,169 | B1 | * | 12/2001 | Bastyr et al. .................. 602/16 |
| 6,413,232 | B1 | * | 7/2002 | Townsend et al. ............. 602/16 |
| 6,527,733 | B1 | * | 3/2003 | Ceriani et al. ................. 602/16 |
| 6,540,709 | B1 | * | 4/2003 | Smits ........................... 602/16 |
| 6,623,439 | B2 | | 9/2003 | Nelson et al. |

(Continued)

*Primary Examiner*—Patricia M Bianco
*Assistant Examiner*—Brandon Jackson
(74) *Attorney, Agent, or Firm*—David E. Heisey; Sheppard Mullin Ritcher & Hampton LLP

(57) ABSTRACT

A knee brace including an adaptable anterior thigh pad for securing an upper portion of the brace to a user's thigh wherein the anterior thigh pad automatically adjusts to underlying soft tissue motion during knee and leg movement. The anterior thigh pad includes a flexible upper horizontal connection and a pair of substantially rigid x-crossing connections. The anterior thigh pad tightens and loosens during normal leg flexing and straightening so as to maintain a tight skeletal grip on the users leg while adapting to thigh muscle movement. The individual straps of the anterior thigh pad connecting the thigh pad to the rigid arms of the knee brace are independently adjustable to accommodate any leg size or shape.

12 Claims, 3 Drawing Sheets

U.S. PATENT DOCUMENTS 6,740,054 B2 * 5/2004 Stearns ................. 602/16
6,890,314 B2 * 5/2005 Seligman ............... 602/26
2004/0267179 A1 * 12/2004 Lerman ................. 602/26

* cited by examiner

KNEE BRACE HAVING AN ADAPTABLE THIGH PAD

FIELD

The field of the invention is orthopedic devices, and more particularly, knee braces.

BACKGROUND

The following includes information that may be useful in understanding the present inventions. It is not an admission that any of the information provided herein is prior art, or relevant, to the presently described or claimed inventions, or that any publication or document that is specifically or implicitly referenced is prior art.

Orthotic devices generally include a substantially rigid biomechanical element that forms the basis of the skeletal support that is required for the majority of these devices, which include braces, supports and splints.

The human knee generally comprises an articulated joint between the thigh and the lower leg muscles that supports the weight of the human body while the person is standing, walking or running. The knee joint is primarily held together by four ligaments; namely, the anterior and posterior cruciate ligaments and the medial and lateral collateral ligaments. The knee joint can be overly weakened by injuries arising out of cartilage damage and ligament strain, which may be caused, by sports injuries, as well as from everyday exercising, or physiological problems such as osteoarthritis. Thus, the human knee is subjected to a variety of stresses and strains particularly during running and jumping movements. Athletes, in particular, are apt to incur a knee injury as a result of a blow to the knee or to a twisting of the knee, which can commonly occur in various contact sports or high stress sports, such as skiing. Normal aging of the knee joint results in diminished knee stability. Muscle control may be reduced; ligaments become lax and thus less effective.

There are a variety of knee braces available on the market or through healthcare providers. These range from braces that tend to totally immobilize the knee to flexible elastic bandages that are intended to provide some flexibility while eliminating lateral movement of the ligaments that support the knee. Some of these are braces intended to be worn as a relatively permanent device for long-term wear or braces that are intended to be worn for a short period of time during overly strenuous for a short period of time, for example, for a weakened knee. The braces have as their primary object to allow for bending and straightening the knee while preventing any unnatural movement, which may aggravate the knee ligaments. While the braces are intended to allow for a natural movement of the knee joint while a person undergoes walking, running, jumping, skating, various other athletic activities, they are intended also to prevent sudden movement of the upper and lower legs to one side or the other and to prevent twisting or rotation of the lower leg relative to the upper leg about the vertical axis.

Typically, the knee braces are held in place by flexible straps, which wrap about the user's thigh and calf above and below the knee, respectively. In this manner, the rigid hinge of the knee brace remains positioned on either side of the user's knee so as to mimic the hinged joint of the knee. However, it is not uncommon for the user's bodily motions to cause the flexible straps to move relative to the person's leg, thereby misaligning the knee brace with respect to the knee. This movement of the brace straps with respect to the user not only cause misalignment and therefore misapplication of the orthotic device, but also cause irritation of the user's skin by this unintended rubbing.

Another problem with knee braces is that they must engage effectively with soft tissue in order to provide the desired support. In many parts of the body the soft tissue will move, for example by expanding or contracting as result of muscle movement. This can cause distal migration of the knee brace with respect to the users leg, which means that the brace is not providing its desired support function. As a soft tissue changes shape, parts of the skin lose contact with the liner of the brace. This reduced contact with the liner can cause the knee brace to lose position, or move relative to the user and therefore become ineffective. The only way of overcoming this problem with existing devices is to tighten the device. This causes discomfort, prevents the skin from breathing, and can irritate the skin about the edges of the device and the liner.

The objective of any rigid knee brace is to exert a predictable force on the user's underlying skeleton. In particular, the objective is to exert a force on the tibia with respect to the femur in the user's body mass above the knee. By definition, knee braces are applied to soft tissue lying between the brace and the user's skeleton. Soft tissue is mobile and moves in a cycle corresponding to a user's gait, whether it be through running, walking or other physical movement common to the human knee. The most mobile soft tissue is the quadriceps mechanism lying in front of the femur in the anterior thigh region.

The central reference point for a knee brace is the knee joint line. In construction, a knee brace would use a rigid joint mechanism that mimics the movement of the knee, which is not just a simple hinge. Because each user's body shape is unique, the exact interface between the knee brace and the user's leg cannot be predetermined in the manufacture of such a device.

The function of the tibial section attached to this joint or central axis is to "fit and grip" the tibia and exert a force on it. In ligament instability bracing is intended to prevent anterior translocation of the tibia with respect to the femur. It is also desired to prevent the tibia deforming into varus (bow legged) or valgus (knock kneed). This is important because often injuries to the collateral ligaments coexist with cruciate ligament related pathology, and resulting instability. In bracing for osteoarthritis the objective is to exert an unloading force on the side of the knee joint most affected by degenerative pathology. This is achieved by "pushing" the tibia into a slight valgus deformity, or less frequently, a slight varus deformity.

The function of the femoral, or thigh portion is to stabilize the central axis, or knee joint, and to provide a lever arm or counteracting force for the tibial section. Ideally the central axis, and attached tibial section, remain in a stable position relative to the actual underlying knee joint. Ideally the "lever arms" extending up the thigh remain in a stable position aligned with the underlying femur.

An improved knee brace is described in applicant's co-pending application entitled "Knee Brace", filed on even date herewith, which application is hereby incorporated by reference herein in its entirety.

Applicant's co-pending application describes a knee brace which can more readily conform to a particular user's leg, such that the straps fit snugly, yet comfortably, about the user's leg adjacent the knee, but yet provide the adequate support so as to prevent relative movement of the knee brace with respect to the knee so that the brace provides its desired function. It would be advantageous to provide a knee brace having, for example, a larger thigh engagement structure.

BRIEF SUMMARY

The inventions described and claimed herein have various attributes and embodiments including, but not limited to, those set forth or described or referenced in this Brief Summary. The inventions described and claimed herein are not limited to or by the features or embodiments identified in this Brief Summary, which is not included for purposes of restriction or limitation.

In one aspect the invention broadly provides a knee brace device having a substantially rigid support and an enlarged adaptable thigh pad providing a better grip on the leg of the user. The thigh pad is connected to rigid elements of the knee brace so as to be correctly aligned with the long axis of the user's femur. The thigh pad includes and x-shaped member which allows the knee brace to spread in leg flexion and narrow in leg extension.

Further aspects of the invention will become apparent from the following detailed description, which is provided by way of example only.

BRIEF DESCRIPTION OF THE DRAWINGS

Various other objects, features and advantages of the present invention will become readily apparent by reading the following description in conjunction with the drawings, which are shown by way of example only, wherein.

DETAILED DESCRIPTION

Figure 1:
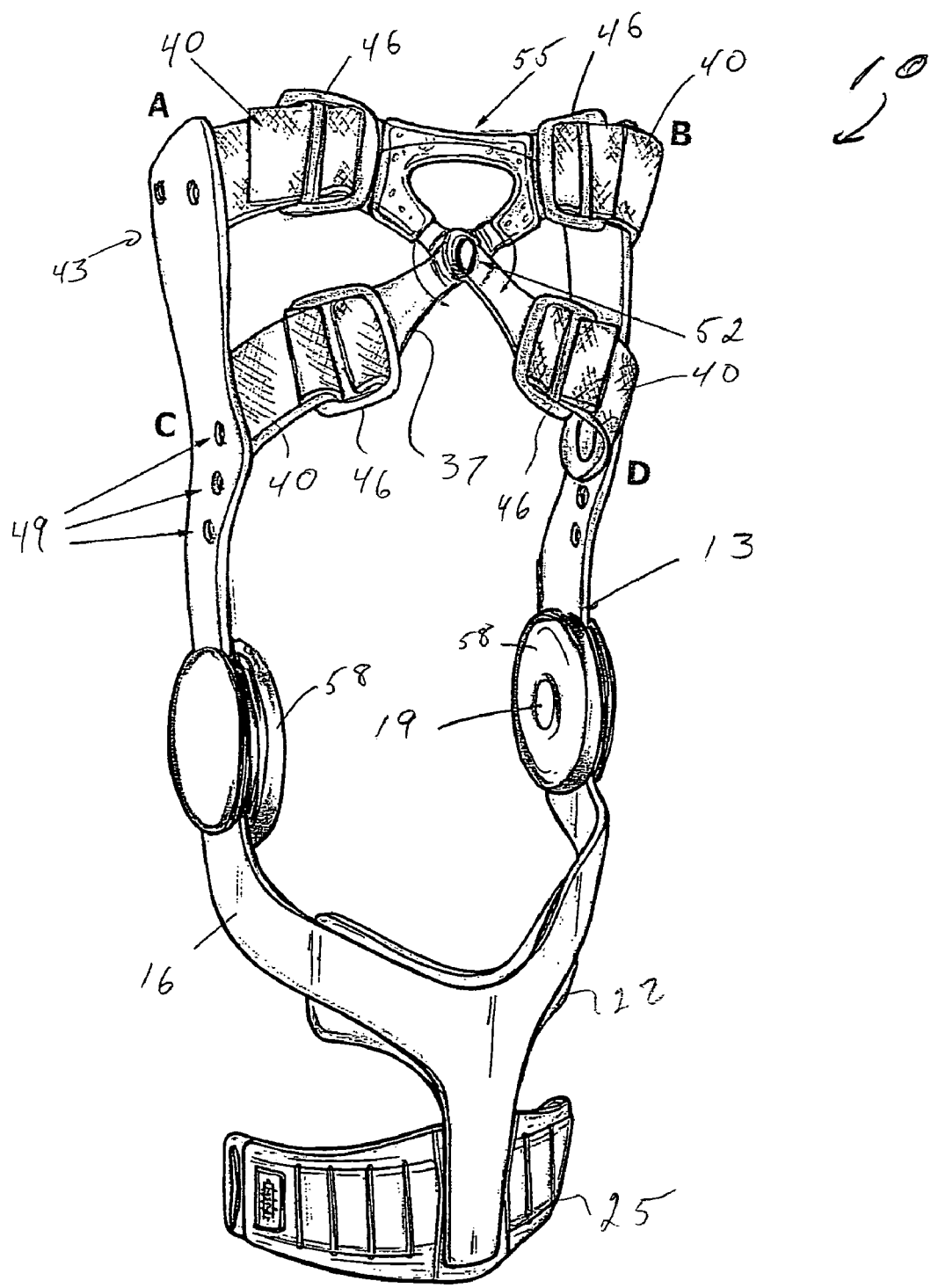
FIG. 1 is a front elevation of a knee brace according to the present invention.

Referring now to the drawings in detail, wherein like reference characters refer to like elements, there is shown in FIG. 1 a knee brace 10 according the present invention. Although this invention will be described by way of example and with reference to various preferred embodiments, it is to be understood that modifications or improvements may be made thereto without departing from the scope or spirit of the invention. Various changes and modifications to the presently preferred embodiments described herein will be apparent to those skilled in the art. Such changes and modifications may be made without departing from the present invention and without diminishing its attendant advantages. It is, therefore, intended that such changes and modifications are included within the present invention.

Referring to FIG. 1, the knee brace 10 is shown having a biomechanical support comprising a pair of substantially rigid upper 13 and lower 16 arms, which are joined together by a hinge assembly 19. Connected to the rigid lower arms is a lower or tibial cuff pad 22 that, together with adjustable tibial strap 25, secures the knee brace 10 to the users lower leg 28 below the knee 31. A second tibial strap (not shown) may be attached to the lower arms 16 adjacent to the tibial cuff 22 to additionally secure the brace 10 in the area of the user's calf.

Preferably, the knee brace 10 is constructed of a relatively strong yet lightweight fiber reinforced composite material. Pads and or liners are used on the interior portion of the brace to provide a comfortable feel against the user's leg. The hinge assembly 19 has a predetermined range of movement corresponding to the desired range of extension and flexion of the user's knee 31.

The upper arms 13 are secured to the users thigh (femur) 34 by an adaptable anterior thigh pad 37. In this way the hinge assembly 19 is placed adjacent the axis of the user's knee joint, thereby allowing the knee brace 10 to substantially mimic the bending of the user's knee 31 as the user goes about his or her otherwise normal activities. The anterior thigh pad 37 is designed to absorb the soft tissue profile change of the thigh, while the brace 10 still exerts a consistent skeletal force for proper support of the knee during normal knee 31 movements. One or more additional straps (not shown) may be used to secure the upper arms 13 to the posterior of the users thigh, in a manner well known in the art.

Figure 2:
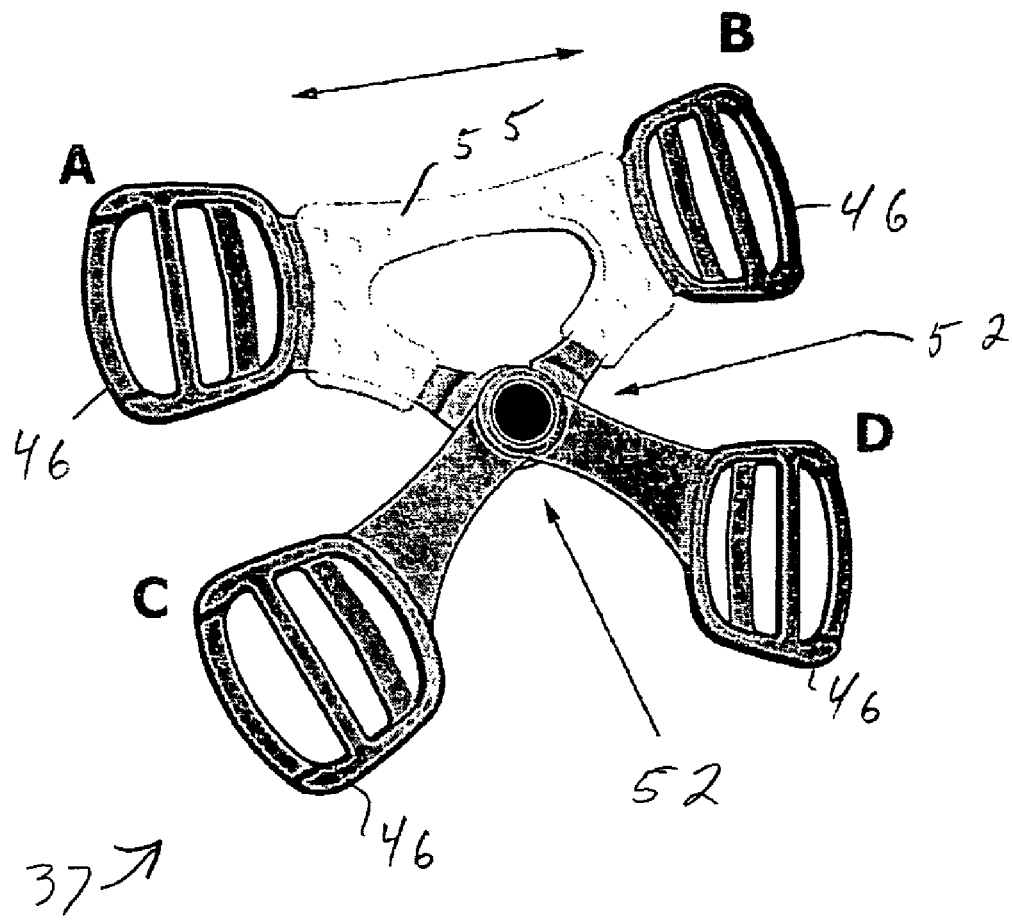
FIG. 2 is a detailed view of an anterior thigh pad for the knee brace according to the present invention.

As indicated in FIGS. 1 and 2, the anterior thigh pad 37 may be attached to the upper arms 13 at four (4) basic attachment points, labeled A, B, C and D. The design of the anterior thigh pad allows the relative position of points A, B, C and D to remain constant, whereas the area in between adapts to underlying soft tissue movement during normal knee motion. The anterior thigh pad 37 is attached to points A, B, C and D are joined by four (4) length-adjustable straps 40. For each of the straps 40 one end 43 is fixed to one of the upper arms 13 while an opposite end passes through a corresponding buckle 46 in the anterior thigh pad and is adjustably secured to itself.

In one most preferred embodiment, it would be advantageous to be able to vary the position of points C and D. For a taller person with a longer thigh 34 it would be beneficial to lower the attachment points C and D, or move them closer to the knee 31. This is achieved by moving the strap attachment point to one of several other predetermined positions 49 on the rigid upper arms 13. A pivot point 52 enables the variable positioning of the straps with respect to points C and D. The pivot point may comprise a rivet or plastic clip.

Preferably the anterior thigh pad 37 is generally constructed of a rigid yet lightweight fiber reinforced composite material similar to that of the upper and lower arms. While the x-crossing members C-B and A-D are integrally formed with their corresponding buckles 46 at points C and D, the upper horizontal connection 55 between points A-B may be accomplished by overmoulding a more resilient thermoplastic resin material. This material in the upper horizontal section 55 of the anterior thigh pad 37 allows for a degree of elasticity and flexibility to accommodate muscle expansion during normal leg movements. However, the rigidity of the crossing members maintains the fixed length of these diagonal sections.

Figure 3:
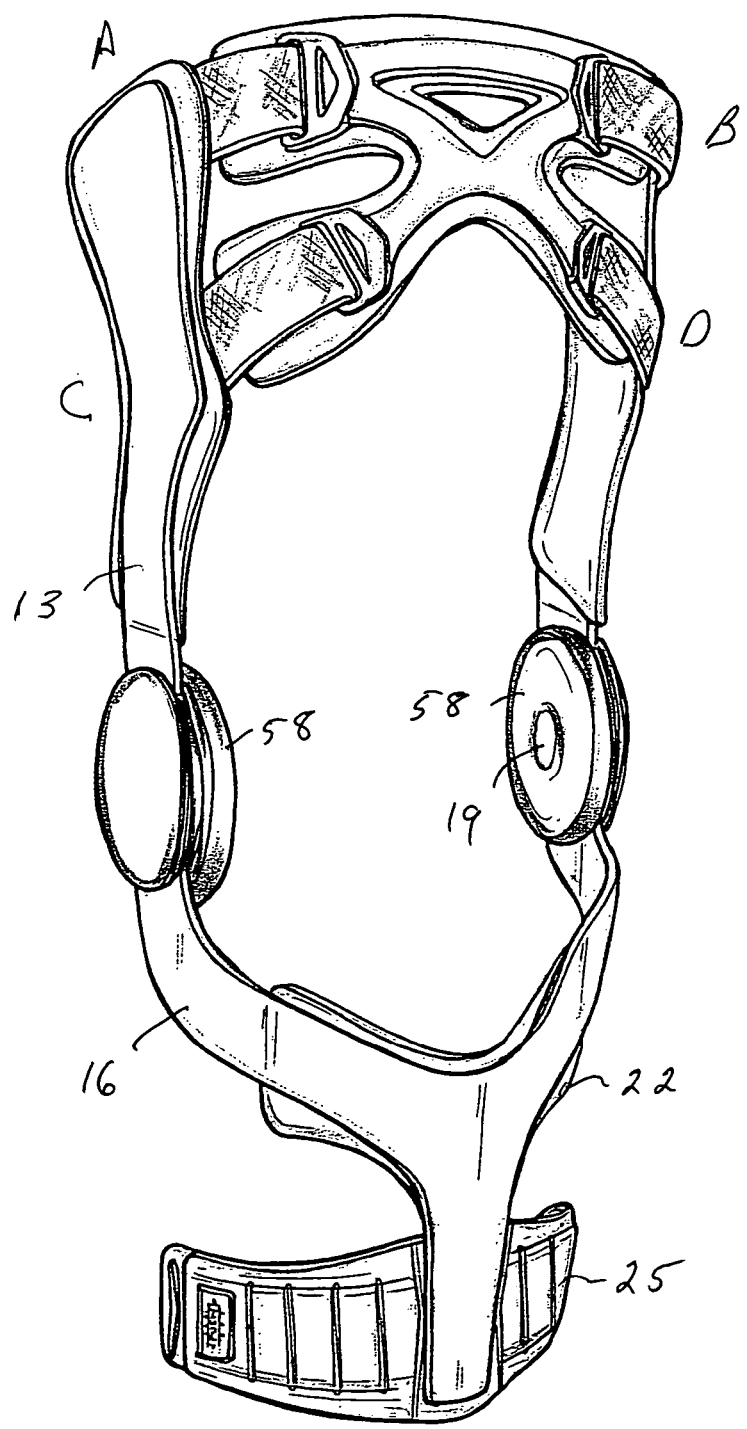
FIG. 3 is a front elevational view of an alternate embodiment of the knee brace according to the present invention.

The anterior thigh pad 37 adapts to the underlying soft tissue movement of the thigh during knee motion. This anterior thigh pad 37 allows the knee brace 10 to spread in leg flexion and narrow in leg extension, just as the leg muscles normally do. This allows the quadriceps and hamstrings of the users upper leg to "fire" normally while the knee brace 10 maintains a predictable and constant force on the skeleton. FIG. 3 shows an alternative embodiment of the thigh pad.

The knee brace of the present invention thus provides a three-point fixation centered at the knee that may be used to achieve the desired control over tibial movement with respect to the femur for proper knee bracing. The knee brace 10 provides a solid grip above the knee, at the knee and below the knee to provide the necessary control of the weakened knee joint. Because the anterior thigh pad 37 for the knee brace 10 of the present invention adapts to the soft tissue movement, distal migration of the knee brace is eliminated. Hence the hinge 19 remains centered at the knee joint. Maintaining the hinge 19 in the proper relation with the knee 31 is desired to "push" the tibia into a slight valgus deformity, or less frequently, a slight varus deformity to counteract anterior translocation of the tibia with respect to the femur which can occur with ligament instability. A condylar pad 58 on the interior portion of each hinge 19 comfortably supports the knee joint in the lateral direction.

The adaptability of the anterior thigh pad 37 for the knee brace 10 of the present invention provides significant advantages over conventional bracing systems. In any population sample there will be a relatively small range of knee width and tibial size, but the range of thigh shape is much greater, and highly variable for any given knee and calf anatomical dimension. For any given individual the thigh shape to which a brace is to be applied will vary with degree of obesity or muscle definition, which tends to vary with exercise. It is therefore preferable to be able to have an adjustable soft or semi-rigid element linking the rigid elements on either side of the thigh. This component must allow for adjustment in several anatomical planes.

The objective of the resilient upper horizontal connection 55 across the top of the anterior thigh pad 37 is to hold the rigid thigh elements in line with the femur and prevent hyperextension (over-straightening) of the knee. The objective of the crossing members is to grip the quadriceps and resist twisting of the knee brace 10, which is important for resistance of certain distorting forces applied to the knee (varus/valgus/rotation).

An objective of the present invention is to provide an adjustable thigh section linking the rigid elements on either side of the thigh, and particularly one that is adjustable in several planes so that a rigid knee brace can be accurately fitted to, and intermittently adjusted for, any anterior thigh anatomical profile. This is beneficial because it allows accurate fitting to a wide range of profiles that can vary over time in any one individual. The human thigh profile is a complicated shape that moves during a gait cycle in a variable way, determined by the relative size of the components of the quadriceps mechanism. The quadriceps is made up of component muscles that vary with activity level in any individual, so changes in overall quadriceps profile are frequent.

Accurate adjustment of the individual straps for the anterior thigh pad 37 of the present knee brace 10 will not only provide an accurate and comfortable fit, but it will ensure that the individual anterior thigh pad 37 is appropriately tensioned to resist distorting forces or movements, and therefore provide a predictable skeletal force. Irrespective of the shape of the tibial component, an anterior thigh component, adjustable in several dimensions, is beneficial in terms of fitting any individual thigh, because it is more adaptive to soft tissue profile. The result is that the knee brace 10 of the present invention is more positionally stable, and therefore exerts a more predictable and constant force on the underlying skeleton, which is the objective of knee bracing.

The instructions for fitting and adjusting the knee brace 10 of the present invention can be easily followed by a user, with or without prior instruction by any health care provider. First, the condylar pads 58 are positioned on each hinge 19 at the knee joint line on either side of the knee. The tibial cuff 22 is generally fitted to the lower leg 28 and the tibial strap(s) 25 tensioned for a firm but not tight fit. The upper arms 13 are thereby positioned on either side of the thigh 34. These should lie in the mid-medial and mid-lateral line parallel to the long axis of the femur. The individual straps 40 of the anterior thigh pad 37 should generally be in a loosened state. The straps connecting the upper horizontal connection between points A and B may be adjusted so that in full extension the upper straps are tight across the thigh 34 and the rigid upper arms 13 lie parallel to the femur in the mid-medial and lateral lines, respectively. With the knee 31 flexed a predetermined amount, preferably at about 30 degrees, the straps connecting points C and D are individually adjusted to give a firm grip across the thigh 34. Preferably, these crossing straps are equally tensioned. When the knee is 31 then straightened, the crossing straps will be in the relaxed state and the horizontal strap will be in a tightened state.

Preferably the knee brace of the present invention provides various pads and liners between the rigid elements and the user's leg, as is conventional with braces in general. Also, a protective cuff or pad may be positioned over the anterior thigh pad 37 to prevent unintentional adjustment of the buckles 49. Such a pad may be attached to the rigid upper arms 13 in any conventional manner, such as, by way of example, with hook and loop fasteners (Velcro).

As can be seen from the foregoing, the invention provides a knee brace that includes functional elements that provides a number of different advantages. One advantage is grip, in terms of gripping the soft tissue of the user in to enable the brace to function effectively, and also to be able to provide skeletal grip in virtually all knee positions.

Where in the foregoing description, reference has been made to specific components or integers of the invention having known equivalents then such equivalents are herein incorporated as if individually set forth. While specific embodiments of the invention have been shown in the drawings and described in detail, it will be appreciated by those skilled in the art that various modifications and alternatives would be developed in light of the overall teachings of the disclosure. Accordingly, the particular arrangements disclosed herein are meant to be illustrative only and not limiting as to the scope of the invention, which is to be given the full breadth of the appended claims and in any and all equivalents thereof.

What is claimed is:

1. A knee brace comprising:
   a lower rigid portion molded to fit on the lower leg of a user;
   a cuff adapted to fit about a tibia of the user;
   upper rigid arms molded to fit on the upper leg of the user;
   a hinge operably connecting the lower rigid portion and the upper rigid arms, such that the hinge is located proximate to the knee of the user; and
   an anterior thigh pad composed of a material that is less rigid than the upper rigid arms connecting the upper arms in such a manner that the anterior thigh pad dynamically adapts to soft tissue movement of the user such that the knee brace maintains a consistent skeletal force, distal migration of the knee brace is eliminated, and the hinge remains proximate to the knee of the user during movement of the user, wherein the anterior thigh pad comprises a generally x-shaped member including a pair of crossing members, at least one crossing member being individually adjustable, connecting the upper rigid arms, a pivot point on a crossing point of the x-shaped member, about which the pair of crossing members rotate at an intersection of the crossing members for adapting to movement of the user, and wherein the anterior thigh pad is adapted to spread in leg flexion and narrow in leg extension;
   wherein the crossing members of the anterior thigh pad are attached to the upper rigid arms at a pair of upper strap attachment points and a pair of lower strap attachment points, wherein a position of the pair of lower attachment points is variable such that the user may select from a range of lower strap attachment points.

2. The knee brace as recited in claim 1, further including a tibial strap adapter to connect the lower arms to the lower leg of the user, and means for adjustably connecting the tibial strap snugly across the user's leg below the knee.

3. The knee brace as recited in claim 2, further including a protective flap secured to the upper rigid arms and adapted to extend across the thigh to cover the anterior thigh pad.

4. The knee brace as recited in claim 1, wherein the anterior thigh pad further comprises a horizontal top member connected between the upper rigid aims and across the top portion of the x-shaped member above the pivot point.

5. The knee brace as recited in claim 1, wherein: the upper rigid arms extend along opposing sides of the upper leg of the user; and the anterior thigh pad includes a rigid assembly and straps that couple the rigid assembly to the upper rigid arms.

6. The knee brace as recited in claim 5, further comprising a tibial cuff connected to the lower rigid portion and adapted to fit snugly about the lower leg of the user.

7. The knee brace as recited in claim 5, further including a protective flap secured to the upper rigid portion and adapted to extend across the thigh to cover the anterior thigh pad.

8. The knee brace as recited in claim 5, wherein the rigid assembly of the anterior thigh pad includes two rigid portions pivotally coupled to each other.

9. The knee brace as recited in claim 8, wherein the rigid portions of the anterior thigh pad are adapted to pivotally spread in leg flexion.

10. The knee brace as recited in claim 8, wherein the rigid portions of the anterior thigh pad are adapted to pivotally narrow in leg extension.

11. The knee brace as recited in claim 8, further comprising a tibial cuff connected to the lower rigid portion and adapted to fit snugly about a lower leg of the user.

12. A knee brace comprising:
a pair of rigid arms having upper and lower portions and a hinge assembly near a midpoint thereof;
a tibial cuff connected to a lower portion of the rigid arm and adapted to fit snugly about a lower leg of the user such that the hinge assembly is adjacent to the user's knee; and
an anterior thigh pad composed of a material that is less rigid than the upper rigid arms for securing the knee brace on an upper leg of the user, wherein the anterior thigh pad is mounted in such a manner as to dynamically conform to movement of the soft tissue of the user's thigh such that the knee brace maintains a consistent skeletal force, distal migration of the knee brace is eliminated, and the hinge assembly remains adjacent to the knee of the user during movement of the user, wherein the anterior thigh pad comprises a generally x-shaped member including a pair of crossing members, at least one crossing member being individually adjustable, connecting the upper portions of the rigid arms, a pivot point about which the pair of crossing members rotate, disposed at an intersection of the crossing members for adapting to movement of the user, and wherein the anterior thigh pad is adapted to spread in leg flexion and narrow in leg extension;
wherein the crossing members of the anterior thigh pad are attached to the upper rigid arms at a pair of upper strap attachment points and a pair of lower strap attachment points, wherein a position of the pair of lower attachment points is variable such that the user may select from a range of lower strap attachment points.

\* \* \* \* \*